US006628409B2

United States Patent
Rotsch

(10) Patent No.: US 6,628,409 B2
(45) Date of Patent: Sep. 30, 2003

(54) METHOD FOR DETERMINING THE DISTANCE BETWEEN PERIODIC STRUCTURES ON AN INTEGRATED CIRCUIT OR A PHOTOMASK

(75) Inventor: Christian Rotsch, München (DE)

(73) Assignee: Infineon Technologies AG, Munich (DE)

( * ) Notice: Subject to any disclaimer, the term of this patent is extended or adjusted under 35 U.S.C. 154(b) by 87 days.

(21) Appl. No.: 10/034,930

(22) Filed: Nov. 21, 2001

(65) Prior Publication Data

US 2002/0149783 A1 Oct. 17, 2002

(30) Foreign Application Priority Data

Nov. 23, 2000 (DE) .......................................... 100 58 216

(51) Int. Cl.[7] .............................................. G01B 11/02
(52) U.S. Cl. ........................................ 356/625; 356/635
(58) Field of Search ................................ 356/625, 630, 356/631, 632, 634, 635, 636, 640, 496, 498, 503; 250/559.24, 559.19, 559.26, 559.27

(56) References Cited

U.S. PATENT DOCUMENTS

| 3,709,610 | A | * | 1/1973 | Kruegle ....................... 356/635 |
| 3,937,580 | A | * | 2/1976 | Kasdan ........................ 356/635 |
| 3,957,376 | A | * | 5/1976 | Charsky et al. ............... 356/496 |
| 4,408,884 | A | * | 10/1983 | Kleinknecht et al. ........ 356/496 |
| 4,636,639 | A | * | 1/1987 | Guillaume et al. ..... 250/559.24 |
| 4,679,941 | A | * | 7/1987 | Fujita .......................... 356/636 |
| 5,361,137 | A | * | 11/1994 | Aton et al. ................... 356/496 |
| 5,422,723 | A | * | 6/1995 | Paranjpe et al. ............. 356/496 |
| 6,020,957 | A |   | 2/2000 | Rosengaus et al. ....... 356/237.4 |
| 6,264,520 | B1 | * | 7/2001 | Yamazaki et al. .............. 445/4 |
| 6,486,954 | B1 | * | 11/2002 | Mieher et al. ............... 356/401 |

FOREIGN PATENT DOCUMENTS

| DE | 100 06 782 A 1 | 8/2001 |
| JP |    62135710 A  | 6/1987 |
| JP |    07128037 A  | 5/1995 |

OTHER PUBLICATIONS

Search Report issued by the German Patent and Trademark Office on Oct. 5, 2001.

* cited by examiner

Primary Examiner—Hoa Q. Pham
(74) Attorney, Agent, or Firm—Laurence A. Greenberg; Werner H. Stemer; Gregory L. Mayback

(57) ABSTRACT

Fourier transformations are used to calculate a power spectrum of an image of an integrated circuit. The distance between periodic structures is determined from the first refraction maximum, which represents the reciprocal of the distance between the periodic structures. This enables performance of a simple method for calculating the distances between the periodic structures on integrated circuits or photomasks.

5 Claims, 2 Drawing Sheets

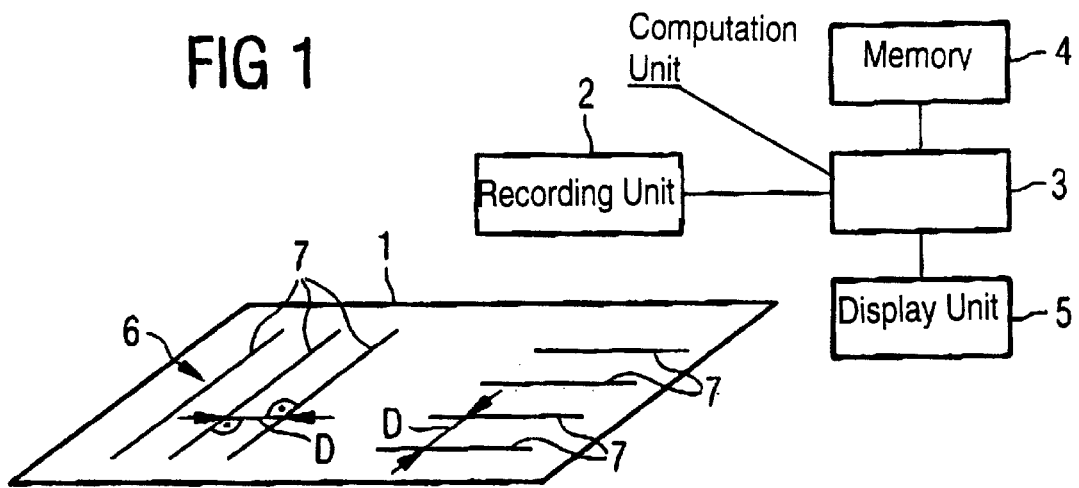
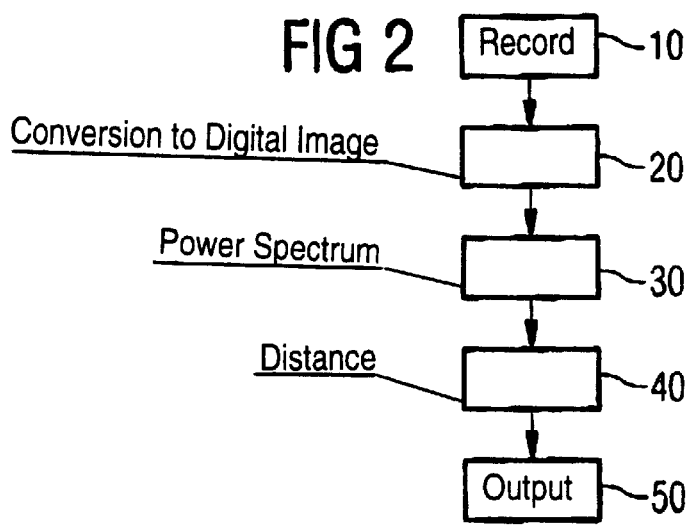
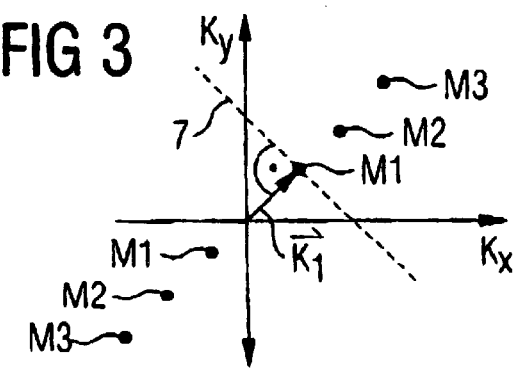

METHOD FOR DETERMINING THE DISTANCE BETWEEN PERIODIC STRUCTURES ON AN INTEGRATED CIRCUIT OR A PHOTOMASK

BACKGROUND OF THE INVENTION

Field of the Invention

The invention relates to a method for determining the distance between periodic structures on an integrated circuit or a photomask in which a map of the integrated circuit or the photomask is recorded.

The mean distance between periodic structures on semiconductor wafers or photomasks is determined by recording measured values for the edge position at a number of measurement points along a structure edge, and by using the measured values to determine the distance between periodic structures on the semiconductor wafer or the photomask.

U.S. Pat. No. 6,020,957 discloses a system and a method for investigating semiconductor wafers in which a number of areas on a semiconductor wafer can be investigated at the same time. In this case, a monochromatic light source is used to illuminate the semiconductor wafer surface. An optical dark-field system gathers the light reflected from the surface of the semiconductor wafer and filters out patterns which correspond to correct periodic wafer structures. In the process, filtering is carried out using the Fourier method. The filtered light is further-processed by a digital signal processor. Defective wafer surfaces are identified by image comparison. However, the known method does not describe any method for determining the distance between periodic structures using Fourier transformation.

A method and an apparatus for recording structure features on a substrate surface are known from Published German Patent Application DE 10 006 782 A1. The method uses the following steps: raising a number of structure features from the rest of the substrate surface, optically recording one surface area of the substrate surface in which at least a number of the raised structure features are located, carrying out the optical recording digitally or in analog form with subsequent digitization, determining at least one mathematical function as a function of the brightness or color steps which alternate regularly on the substrate surface, and determining the amplitude spectrum of that function. The amplitude spectrum of that function is obtained by Fourier analysis.

SUMMARY OF THE INVENTION

It is accordingly an object of the invention to provide a method for determining the distance between periodic structures on integrated circuits or photomasks.

With the foregoing and other objects in view there is provided, in accordance with the invention, a method for determining the distances between periodic structures on an integrated circuit or on a photomask, that includes steps of: recording a map selected from the group consisting of a map of an integrated circuit and a map of a photomask; calculating a Fourier Transform of the map; determining a first-order maximum and a zero-order maximum in the Fourier transform; and calculating a distance between the periodic structures on the integrated circuit or the mask from a distance between the zero-order maximum and the first-order maximum.

In accordance with an added feature of the invention, the method includes: calculating a power spectrum from the Fourier transform; and performing the step of calculating the distance between the periodic structures using a distance between a first-order maximum and a zero-order maximum in the power spectrum.

In accordance with an additional feature of the invention, the method includes evaluating the power spectrum to determine an orientation of one of the periodic structures.

In accordance with another feature of the invention, the method includes: integrating the power spectrum along different straight lines that run through the zero-order maximum; and identifying one of the straight lines, having an integral that is greater than that of all others of the straight lines, as an orientation axis; the one of the periodic structures being configured at an angle of 90° with respect to the orientation axis.

In accordance with a further feature of the invention, the method includes: producing the map in a form selected from the group consisting of an optical image and a digital image.

One major step in the invention is for a map of the periodic structure to be recorded, and to be subjected to Fourier transformation. The distance between the periodic structures is determined from the position of the first-order maximum in the Fourier spectrum. This provides a simple way for obtaining and evaluating overall information relating to the recorded structure.

A power spectrum is advantageously calculated utilizing the Fourier transformation, and the distance between the periodic structures is calculated from the distance between the first-order maximum and the zero-order maximum of the power spectrum. The use of the power spectrum offers a simple and reliable method, by means of which it is possible to determine the distances between the periodic structures precisely.

It is also advantageous to determine the orientation of the periodic structure by integration of the power spectrum.

The orientation of the periodic structure is preferably obtained by integrating the power spectrum along different straight lines that run through the zero-order maximum and by selecting the straight line whose integral has the greatest value as the orientation axis. This orientation axis is configured at an angle of 90° with respect to the periodic structure. The orientation of the periodic structure can be determined precisely by means of the described method.

Depending on the embodiment, the map of the periodic structure can be produced in the form of an optical image or in the form of a digital image, and can be evaluated in an appropriate manner.

Other features which are considered as characteristic for the invention are set forth in the appended claims.

Although the invention is illustrated and described herein as embodied in a method for determining the distance between periodic structures on an integrated circuit or a photomask, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 schematically shows a test layout for carrying out the method;

FIG. 2 is a flowchart of the method;

FIG. 3 is schematic illustration of a power spectrum; and

DESCRIPTION OF THE PREFERRED EMBODIMENTS

Figure 4:
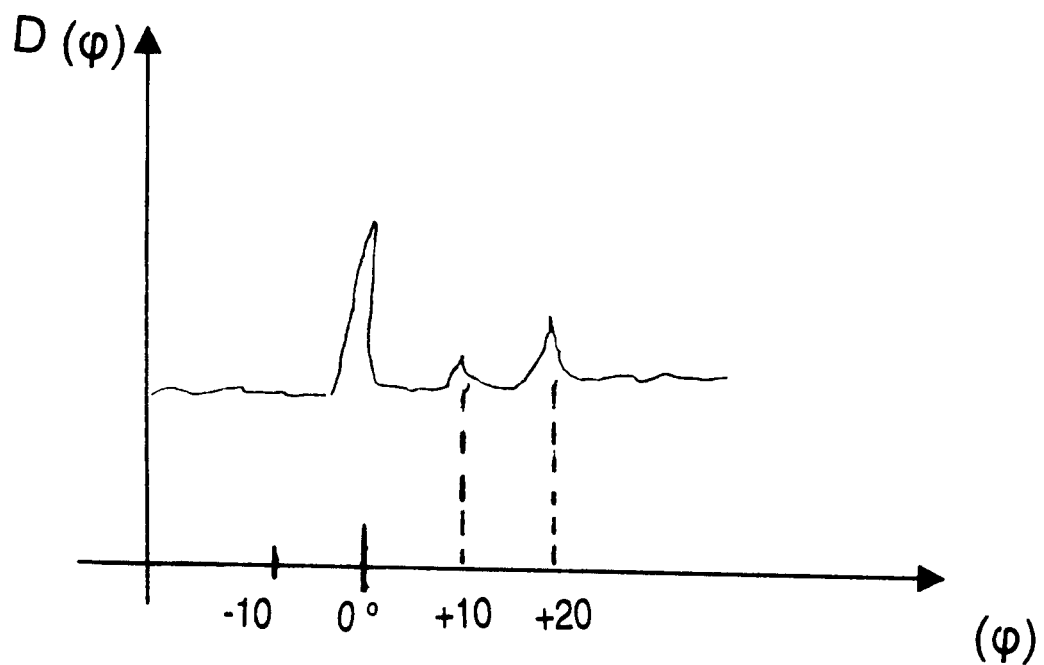
FIG. 4 is a graph with the orientation of a power spectrum.

FIG. 1 shows a measurement object 1, with which a recording unit 2 is associated. The recording unit 2 is connected to a computation unit 3. The computation unit 3 is connected to a memory 4 and to a display unit 5. The recording unit 2 can be, for example, an optical camera, a scanning electron microscope, or an optical microscope. The function of the recording unit 2 is to record the structure in the form of a map. The nature of the map may be chosen depending on the application.

The recording unit 2 may have both a light receiving unit and a light emitting unit. A light-sensitive sensor such as a CCD (Charge-Coupled Device) semiconductor module or a CMOS (Complementary Metal Oxide Semiconductor) photodiode is used, for example, as the light receiving unit. A monochromatic light source, such as for example, a semiconductor laser, or alternatively any other type of light source, may be used to illuminate the surface of the measurement object 1.

A semiconductor wafer with an integrated circuit, or a photomask, is arranged as the measurement object 1. Both the integrated circuit on the semiconductor wafer and the exposed structures of the photomask have periodic structures, which are illustrated schematically in the form of parallel edges 7 in FIG. 1. In modern integrated circuit production methods, it is necessary to accurately set the distance between edges 7 of periodic structures. This is done by determining the distances using a test procedure, and by comparing them with predetermined distances. If there are any discrepancies, then a correction is carried out. Periodic structures include, for example, edges 7 of gate contacts for transistors or contact hole edges, for example, for deep trench technology.

The recording unit 2 records, as the map, the surface 6 of the measurement object 1, and supplies the map to the computation unit 3. The computation unit 3 digitizes the recorded map, and subjects the digital map to Fourier transformation. During the Fourier transformation, a power spectrum is calculated using known methods. The methods for calculating the Fourier transformation and the power spectrum are stored in the form of computer programs in the memory 4. The way in which a Fourier transformation, such as the Fast Hartley Transform (FHT), is carried out, is described by R. N. Bracewell, Proc. IEEE Vol. 72, 8 (1984).

The power spectrum that is obtained corresponds, in a simple form, to a sequence of maxima, which are arranged on a straight line. By way of example, FIG. 3 shows a corresponding power spectrum. The computation unit 3 now determines the distance d between the center point of the power spectrum and the first-order maximum M1. The distance between the center point and the first-order maximum corresponds to the reciprocal of the distance D between periodic structures ($D=2\pi/d$). The computation unit 3 determines the distance between the periodic structures, and outputs this distance via the display unit 5. The edges 7 bound, for example, contact surfaces, interconnects, gate connection surfaces, etc.

In one preferred embodiment, a calibration sample having structures with known periodic distances between the edges is used as the measurement object 1 in another application. In this case, the recording unit 2 is used to record a map of the calibration sample, which is subjected to Fourier transformation by the computation unit, and the position of the first-order maximum in the power spectrum is compared with the known periodic distances. The power spectrum is stretched or compressed until the distance between the first-order maximum and the center point corresponds to the known distance. The power spectrum is calibrated for known distances in this way.

FIG. 2 schematically shows the program sequence for carrying out the method. In program item 10, the recording unit 2 records an optical image of the surface of the measurement object 1 in the form of a gray-scale distribution $(t_B(x,y))^2$, with $t_B$ representing the gray-scale of a point, and x, y representing the coordinates of that point. The gray-scale distribution is normalized to the range between [0,1]. From the gray-scale distribution, the computation unit 3 uses a Fourier transformation to calculate the Fourier spectrum $t_F$ of the gray-scale distribution resulting in $(t_F(Kx,Ky))^2$, with the Fourier spectrum being normalized to the range between 0 and 1. The power spectrum is obtained from the equation $\log t_F^2 = 2 \log t_F$. The power spectrum is obtained from the previous equation using the following formula:

$$t_F(Kx,Ky) = \int\int t_B(X,Y) e^{-i(KxX+KyY)} dX dY$$

where $\overline{K}=(Kx,Ky)$ is the reciprocal grating vector. The direction of the reciprocal grating vector $\vec{K}$ indicates the orientation of the periodic structure, and the magnitude indicates the distance between the periodic structures. $\vec{K}_1$ denotes the vector from the zero-order maximum to the first-order maximum in the power spectrum. The periodic distance D between the periodic structures is given by:

$$D = \frac{2\pi}{|\vec{K}_1|}$$

The distance between the periodic structures is thus calculated from the vector $\vec{K}_1$.

The optical image is transmitted to the computation unit 3 for this purpose. The computation unit 3 converts the analog image to a digital image in program item 20. In the next program item 30, the computation unit 3 applies the Fourier transformation to the digital image, and uses the digital image to calculate a power spectrum in accordance with the formula quoted above.

In the next program item 40, the computation unit 3 records the vector $K_1$ between the first-order maximum and the zero-order maximum in the power spectrum. The computation unit 3 then calculates the distance D between the periodic structures:

$$D = \frac{2\pi}{|\vec{K}_1|}$$

In the next program item 50, the computation unit 3 outputs the determined distance D between the periodic structures via the display unit 5.

FIG. 3 schematically shows a simple power spectrum. FIG. 3 shows a reciprocal grating space, which is represented in the form of two grating vectors kx, ky. Intensity maxima M1, M2, M3 are shown on a straight line, having been calculated as the power spectrum by means of Fourier transformations. The vector $K_1$ between the first-order maximum M1 and the center point at which the zero-order maximum is arranged is proportional to the reciprocal of the value of the distance D between the periodic structures on the surface 6 of the measurement object 1. The orientation of one edge 7 in a periodic structure is at an angle of 90° to the vector $K_1$.

One major aim of the invention is to determine the periodicity of structures in integrated circuits on semiconductor wafers or on photomasks which are used for exposing etching photoresists during the production of integrated circuits, in a simple manner. The described method offers the advantage that all of the image information is used in order to determine the periodic distance D. The periodic distance is therefore determined precisely.

It is also advantageous to evaluate the power spectrum in order to find out the orientation of the periodic structures. To do this, via the intensity of the power spectrum, the power spectrum is integrated along a number of straight lines which run through the center point of the power spectrum. Since the power spectrum has considerably higher intensity values at the maxima than in other image areas, the optimum straight line is found when the integral D ($\psi$) is a maximum. If the intensity at a point ($K_x$, $K_y$) in the power spectrum is denoted by I ($K_x$, $K_y$), and the angle $\psi$ is chosen as the straight line parameter, then the integral D($\psi$), normalized with respect to intensities, can be calculated along a straight line.

FIG. 4 schematically shows the illustration of the integrated power spectrum D($\psi$) in which the structure in the angle region around 0° can clearly be seen, for orientation. The periodic structures are thus arranged at an angle of 90° to the 0° direction, that is to say the vector $K_1$ points in the 0° direction.

In one simple embodiment, the zero-order maximum and the first-order maximum are determined from the Fourier spectrum of the gray-scale distribution $t_F(K_x, K_y)$, and are used for determining the distance between periodic structures.

I claim:

1. A method for determining distances between periodic structures on an integrated circuit or on a photomask, which comprises:

recording a map selected from the group consisting of a map of an integrated circuit and a map of a photomask;

calculating a Fourier Transform of the map;

determining a first-order maximum and a zero-order maximum in the Fourier transform; and calculating a distance between periodic structures, on a component selected from the group consisting of the integrated circuit and the photomask, from a distance between the zero-order maximum and the first-order maximum.

2. The method according to claim 1, which comprises:

calculating a power spectrum from the Fourier transform; and performing the step of calculating the distance between the periodic structures using a distance between a first-order maximum and a zero-order maximum in the power spectrum.

3. The method according to claim 2, which comprises evaluating the power spectrum to determine an orientation of one of the periodic structures.

4. The method according to claim 3, which comprises:

integrating the power spectrum along different straight lines that run through the zero-order maximum; and identifying one of the straight lines, having an integral that is greater than that of all others of the straight lines, as an orientation axis; the one of the periodic structures being configured at an angle of 90° with respect to the orientation axis.

5. The method according to claim 1, which comprises producing the map in a form selected from the group consisting of an optical image and a digital image.

* * * * *